(12) United States Patent
Miclaus et al.

(10) Patent No.: US 11,768,122 B2
(45) Date of Patent: *Sep. 26, 2023

(54) LIQUID DETECTION IN A SENSOR ENVIRONMENT AND REMEDIAL ACTION THEREOF

(71) Applicant: InvenSense, Inc., San Jose, CA (US)

(72) Inventors: Calin Miclaus, Fremont, CA (US); Chung-Hsien Lin, Hsinchu City (TW); Jye Ren, Taipei City (TW); Tim Piessens, Bornem (BE); Pei-Wen Yen, Hsinchu City (TW); Manish Sharma-Kulamarva, Chandler, AZ (US)

(73) Assignee: InvenSense, Inc., San Jose, CA (US)

( * ) Notice: Subject to any disclaimer, the term of this patent is extended or adjusted under 35 U.S.C. 154(b) by 36 days.

This patent is subject to a terminal disclaimer.

(21) Appl. No.: 17/964,501

(22) Filed: Oct. 12, 2022

(65) Prior Publication Data
US 2023/0035487 A1    Feb. 2, 2023

Related U.S. Application Data

(63) Continuation of application No. 16/518,879, filed on Jul. 22, 2019, now Pat. No. 11,499,884.

(60) Provisional application No. 62/702,861, filed on Jul. 24, 2018.

(51) Int. Cl.
| | | |
|---|---|---|
| *G01N 25/56* | (2006.01) | |
| *G01N 27/12* | (2006.01) | |
| *G01L 19/06* | (2006.01) | |
| *G01L 19/00* | (2006.01) | |
| *G01L 9/00* | (2006.01) | |
| *G01N 27/22* | (2006.01) | |
| *G01N 27/04* | (2006.01) | |

(52) U.S. Cl.
CPC .......... *G01L 19/0654* (2013.01); *G01L 9/0041* (2013.01); *G01L 19/0092* (2013.01); *G01N 25/56* (2013.01); *G01N 27/048* (2013.01); *G01N 27/223* (2013.01)

(58) Field of Classification Search
None
See application file for complete search history.

(56) References Cited

U.S. PATENT DOCUMENTS

2021/0072176 A1*   3/2021   Han et al. .............. G04G 21/02

* cited by examiner

*Primary Examiner* — Herbert K Roberts

(57) ABSTRACT

A device includes a housing unit with an internal volume. The device further includes a sensor coupled to a substrate via an electrical coupling, wherein the sensor is disposed within the internal volume of the housing unit, and wherein the sensor is in communication with an external environment of the housing unit from a side other than a side associated with the substrate. The device also includes a moisture detection unit electrically coupled to the sensor, wherein the moisture detection unit comprises at least two looped wires at different heights, and wherein the moisture detection unit is configured to detect presence of a moisture within an interior environment of the housing unit when the moisture detection unit becomes in direct contact with the moisture.

21 Claims, 8 Drawing Sheets

LIQUID DETECTION IN A SENSOR ENVIRONMENT AND REMEDIAL ACTION THEREOF

RELATED APPLICATIONS

The instant application is a continuation patent application and claims the benefit and priority to a U.S. Application 16/518,879 filed on Jul. 22, 2019, which claims the benefit and priority to the U.S. Provisional Application 62/702,861 filed on Jul. 24, 2018, which are incorporated herein by reference in their entirety.

BACKGROUND

Many electronic devices are used in various conditions and are exposed to different external environments. For example, sensors may come in contact with the external environment such as water, oil, and other liquids, etc., that may be damaging to the sensing device. Conventionally, the package cavity of the electronic device is increased and filled with gel to protect the electronic device from exposure to external liquid and gas. Filling the package cavity with gel protects the electronic devices, such as sensors but unfortunately falls short of taking any remedial action to remove the unwanted liquid. Moreover, there are no mechanisms to detect whether unwanted liquid is present and to take further remedial actions. The unwanted liquid may further impact the performance of many electronic devices, such as sensors, by adding an offset due to increase mass and pressure created by the unwanted liquid.

SUMMARY

Accordingly, a need has arisen to protect the electronic device from being exposed to the external environment, e.g., water, gas, etc., and to detect presence of liquid. Moreover, a need has arisen to take remedial actions, e.g., removal of the unwanted liquid, in response to detecting presence of unwanted liquid.

In some embodiments, a device includes a sensor die, an electrical coupling, a substrate, a liquid detection unit, and a housing unit. The sensor die is coupled to the substrate via the electrical coupling. The liquid detection unit electrically is coupled to the sensor die. The housing unit and the substrate are configured to house the sensor die, the liquid detection unit, and the electrical coupling. The housing unit comprises an opening that exposes the sensor die to an environment external to the housing unit. The liquid detection unit is configured to detect presence of liquid within an interior environment of the housing unit. In some embodiments, the device further includes a gel filled within the interior environment of the housing unit covering the sensor die and the substrate. The gel, e.g., silicone, fluoro silicone, etc., is configured to protect the sensor die, the electrical coupling, and the substrate from exposure to the liquid.

According to some embodiments, the liquid detection unit comprises electrodes, which detects presence of liquid responsive to a change in thermal conductance measured by the electrodes. It is appreciated that the change in the thermal conductance is measured by measuring a resistance between the electrodes and by comparing the measured resistance to a resistance between the electrodes in absence of the liquid. It is appreciated that in some embodiments, the electrodes measure a capacitance between the electrodes and presence of liquid is detected by detecting a change between the measured capacitance and a capacitance between the electrodes in absence of liquid.

In some embodiments, the liquid detection unit transmits the measured capacitance to the sensor die for processing and determining whether liquid is present. According to some embodiments, the liquid detection unit is within the sensor die and is configured to detect presence of liquid by detecting a change in a measured electrical characteristics by the electrodes.

Moreover, it is appreciated that the device may further include a heating element configured to generate heat. The liquid detection unit comprises a temperature sensor and the liquid detection unit is configured to measure an amount of time elapsed until the temperature sensor determines that a predetermined temperature is reached. Furthermore, presence of liquid is detected responsive to a difference between the amount of time elapsed as measured by the liquid detection circuitry and an amount of time elapsed to reach the predetermined temperature in absence of liquid is greater than a threshold.

In some examples, the sensor die may be a pressure sensor. It is appreciated that in some embodiments, the liquid detection unit comprises a plurality of looped wires where at least two looped wires of the plurality of looped wires are at different heights. Accordingly, a pair of looped wires of the plurality of looped wires at a first height is configured to detect a different amount of liquid presence from another pair of looped wires of the plurality of looped wires at a second height. Moreover, it is appreciated that the liquid detection unit is configured to detect presence of liquid responsive to detecting a change in output from the sensor die to a calibrated model.

In some embodiments, a device includes a sensor die comprising a heating element, a substrate electrically coupled to the sensor die, a liquid detection unit electrically coupled to the sensor die, and a housing unit comprising an opening that exposes the sensor die to an environment external to the housing unit. The housing unit and the substrate are configured to house the sensor die and the liquid detection unit. The liquid detection unit is configured to detect presence of liquid within an interior environment of the housing unit. In some embodiments, the liquid detection unit is configured to measure a change in permeability. A control circuitry within the sensor die is configured to turn on the heating element responsive to the liquid detection circuitry detecting presence of liquid. The control circuitry is configured to turn the heating element on and maintain a temperature at a predetermined temperature responsive to the liquid detection unit determining that liquid is present until the liquid detection unit determines absence of liquid. It is appreciated that applying heat responsive to detecting presence of water evaporates the water from the housing unit. In some embodiments, the control circuity turns the heating element on to maintain a predetermined temperature in response to detecting that output from the sensor die has drifted, and therefore maintaining the predetermined temperature compensates for the drift.

In some embodiments, the device is the interior environment of the housing unit is filled with a gel covering the sensor die and the substrate. The gel is configured to protect the sensor die and the substrate from exposure to the liquid. In some embodiments, the sensor die comprises a pressure sensor and the heating element is disposed in a plane of a movable membrane of the pressure sensor. In some illustrative examples, the heating element is disposed around the movable membrane. The heating element may include silicon in some examples.

These and other features and aspects of the concepts described herein may be better understood with reference to the following drawings, description, and appended claims.

DETAILED DESCRIPTION

Before various embodiments are described in greater detail, it should be understood by persons having ordinary skill in the art that the embodiments are not limiting, as elements in such embodiments may vary. It should likewise be understood that a particular embodiment described and/or illustrated herein has elements which may be readily separated from the particular embodiment and optionally combined with any of several other embodiments or substituted for elements in any of several other embodiments described herein.

It should also be understood by persons having ordinary skill in the art that the terminology used herein is for the purpose of describing the certain concepts, and the terminology is not intended to be limiting. Unless indicated otherwise, ordinal numbers (e.g., first, second, third, etc.) are used to distinguish or identify different elements or steps in a group of elements or steps, and do not supply a serial or numerical limitation on the elements or steps of the embodiments thereof. For example, "first," "second," and "third" elements or steps need not necessarily appear in that order, and the embodiments thereof need not necessarily be limited to three elements or steps. It should also be understood that, unless indicated otherwise, any labels such as "left," "right," "front," "back," "top," "middle," "bottom," "forward," "reverse," "clockwise," "counter clockwise," "up," "down," or other similar terms such as "upper," "lower," "above," "below," "vertical," "horizontal," "proximal," "distal," and the like are used for convenience and are not intended to imply, for example, any particular fixed location, orientation, or direction. Instead, such labels are used to reflect, for example, relative location, orientation, or directions. It should also be understood that the singular forms of "a," "an," and "the" include plural references unless the context clearly dictates otherwise.

Unless defined otherwise, all technical and scientific terms used herein have the same meaning as commonly understood by persons of ordinary skill in the art to which the embodiments pertain.

As described above, a need has arisen to protect the electronic device from being exposed to the external environment, e.g., water, gas, etc., and to detect presence of liquid. Moreover, a need has arisen to take remedial actions, e.g., removal of the unwanted liquid, in response to detecting presence of unwanted liquid.

Figure 1:
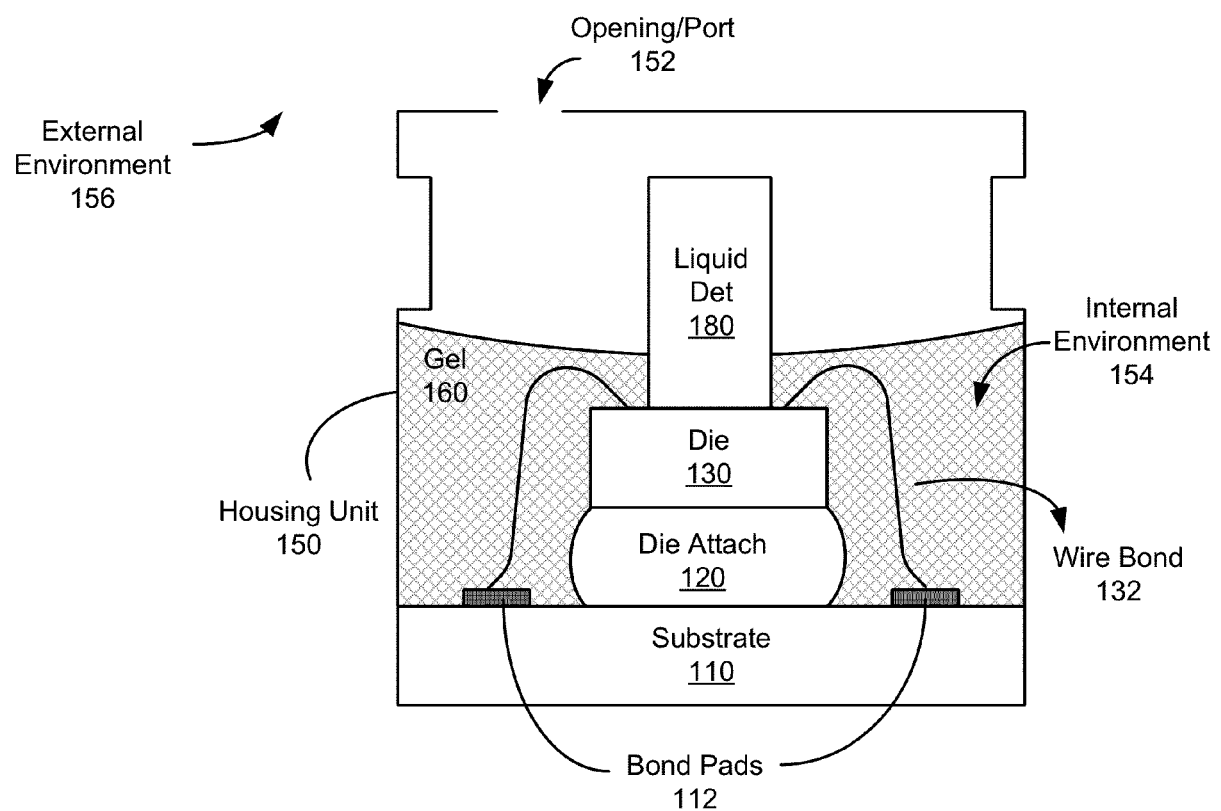
FIG. 1 shows a device including a liquid detection unit in accordance with some embodiments.

FIG. 1 shows a device including a liquid detection unit in accordance with some embodiments. The device includes a substrate 110 and a die 130 that is attached to the substrate 110 using a die attach material 120. Die attached material 120 provides mechanical attachment. Die attach material 120 may be any one of e.g., soft adhesive, soft silicon glue, roomtemperature-vulcanizing (RTV) silicone, epoxy, etc. In some embodiments the substrate can be a printed circuit board (PCB) or similar package substrate. It is appreciated that in some embodiments, the die 130 may be electrically coupled to the substrate 110 using electrical coupling. The die 130 may be a sensor, e.g., pressure sensor, temperature sensor, microphone sensor, etc. It is appreciated that according to some embodiments the die 130 is an integrated sensor and CMOS die. In other embodiments, CMOS die can be a separate die either bonded to sensor die or a discrete die disposed in the housing unit 150. In this embodiment, the electrical coupling is via wire bond 132 that electrically couples the die 130 to the bond pads 112 positioned on the substrate 110. The housing unit 150 may be attached to the substrate 110 to form a housing for the die 130. In some embodiments, the housing unit 150 is attached to the substrate 110 via attach material, e.g., solder, epoxy glue, etc. The housing unit 150 may include an opening 152 that exposes the die 130 to the external environment 156 of the device even though the die 130 is positioned within the internal environment 154 of the housing unit 150. It is appreciated that in some embodiments, the housing unit 150 may be a packaging container for housing the electronic components, e.g., sensor, die, etc., therein.

It is appreciated that in order to protect the device and electronic components within from the external environment, e.g., liquid such as water or oil, gas, etc., the internal environment 154 may be filled with gel 160, e.g., silicone and fluoro silicone. It is appreciated that the gel may be a pressure transmitting dielectric.

It is appreciated that in the illustrated embodiment, the housing unit 150 coupled to the substrate 110 forms a housing for the electronic components therein. However, it is appreciated that in some embodiments, the housing unit 150 may further house and hold the exterior surfaces, e.g., bottom surface, side surfaces, etc., of the substrate 110 (not shown here).

The device further includes a liquid detection unit 180 that detects presence of unwanted liquid within the internal environment 154 of the housing unit 150. It is appreciated that in some embodiments, the liquid detection unit 180 detects the presence of unwanted liquid, e.g., water, oil, etc., by measuring the thermal conductance changes. For example, thermal conductance may be higher when unwanted liquid is present. In some embodiments, the liquid detection unit 180 may detect the presence of unwanted liquid by measuring a change in impedance. For example, the impedance (i.e. resistance) may change when unwanted liquid is present in comparison to when unwanted liquid is absent. In some embodiments, the resistance may be measured by the liquid detection unit 180 at different voltages and the measured values may be fitted to a voltage-current curve where the second order of the coefficient is an indication of thermal conductivity to the environment. In some embodiments, the thermal conductance is higher in presence of unwanted liquid.

It is appreciated that in some embodiments, the liquid detection unit 180 may detect the presence of unwanted liquid by measuring a change in capacitance. For example, the capacitance value may change when unwanted liquid is present in comparison to when unwanted liquid is absent. In other words, according to some illustrative embodiments, the liquid detection unit 180 may detect presence of unwanted liquid by measuring a change in electrical characteristics, e.g., impedance, capacitance, etc. In some embodiments, the liquid detection unit 180 may include a heating element to generate heat and may detect presence of unwanted liquid by applying a predetermined temperature, e.g., 10° C., and using a temperature sensor to measure the amount of time that it takes for the temperature sensor to measure a predetermined temperature and comparing it to the amount of time that it takes to measure the predetermined temperature in absence of the unwanted liquid. If the difference in the amount of time is greater than a threshold then the liquid detection unit 180 may determine that unwanted liquid is present. In some embodiments, the liquid detection unit 180 is configured to detect presence of liquid responsive to detecting a change in output from the sensor die 130 to a calibrated model. It is appreciated that the liquid detection unit 180 may transmit the measured value(s) to the die 130 for processing.

Figure 2A:
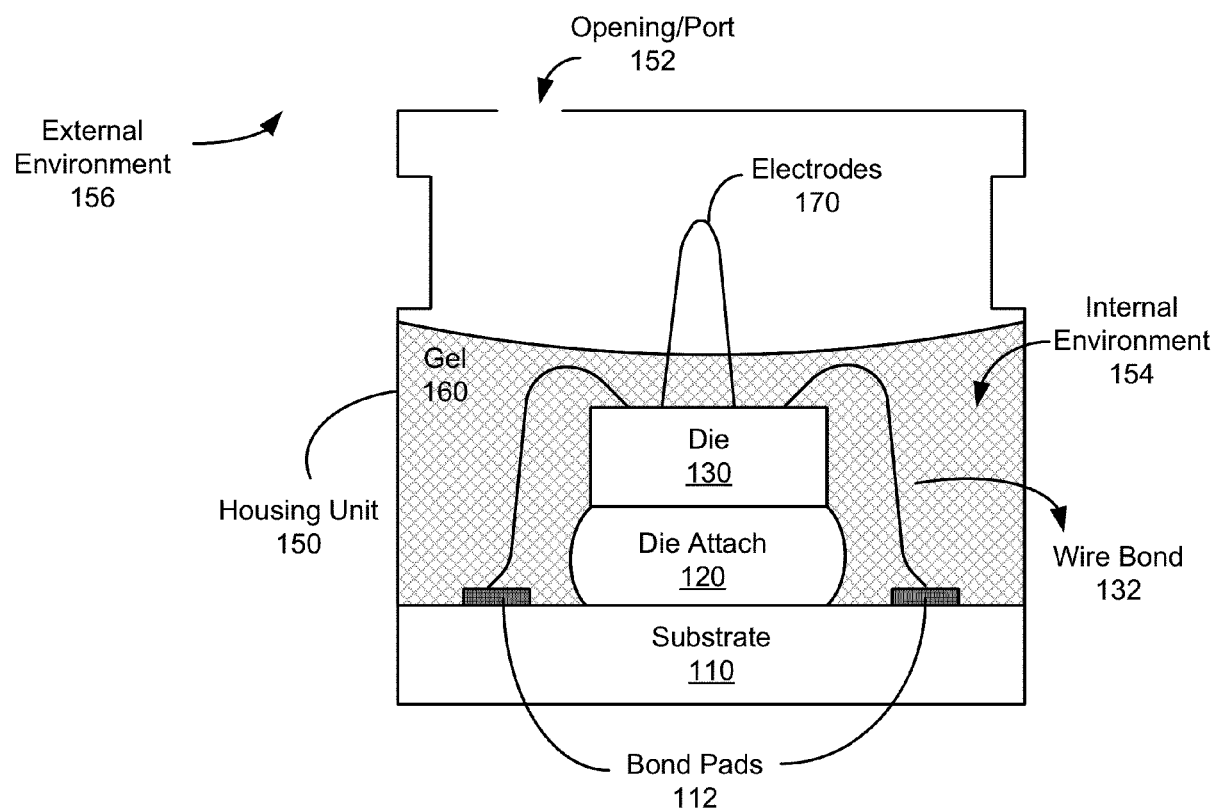
FIGS. 2A-2B show devices with electrodes for detecting presence of liquid in accordance with some embodiments.
Figure 2B:
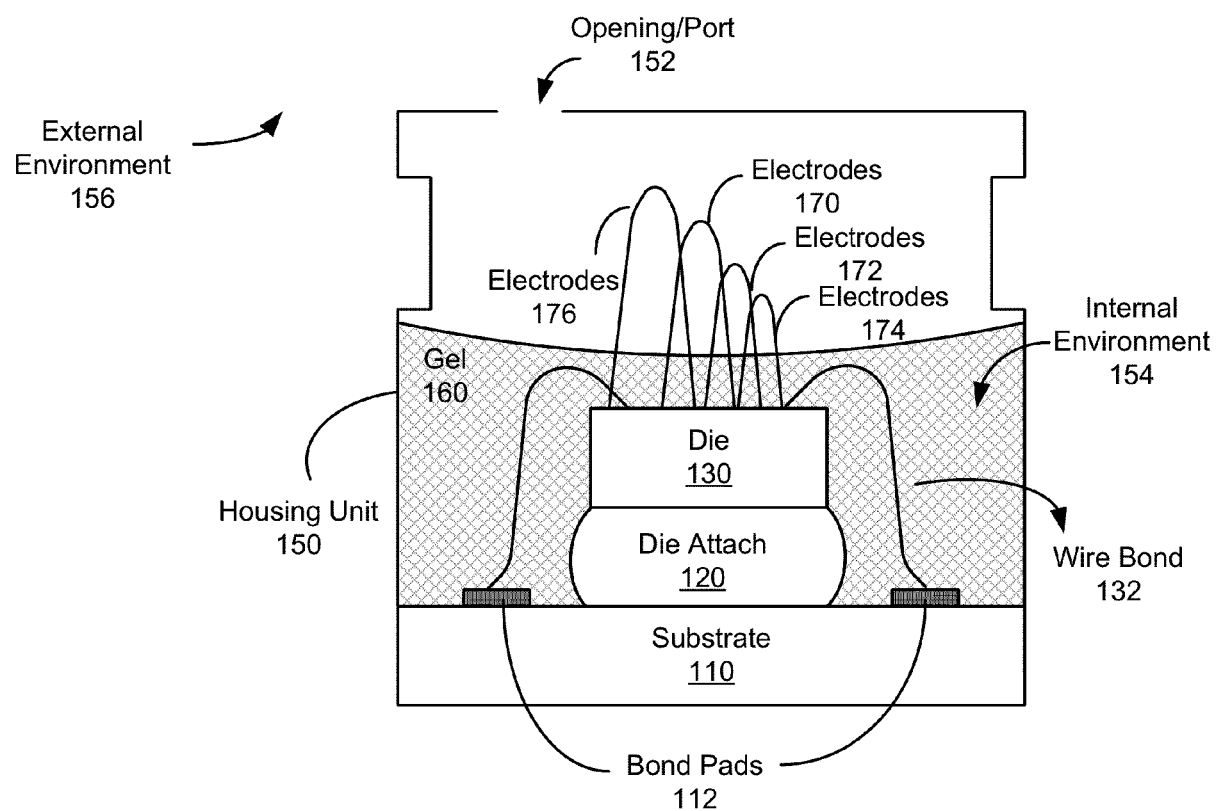

Referring now to FIGS. 2A-2B, devices with electrodes for detecting presence of liquid in accordance with some embodiments are shown. Referring specifically to FIG. 2A, a device similar to that of FIG. 1 is shown. In this embodiment, the liquid detection unit 180 of FIG. 1 includes electrodes 170 that detect presence of liquid, e.g., unwanted liquid, within the internal environment 154 of the housing unit 150. In some embodiments, the electrodes 170 may be a pair of loop wires separated by a gap and sharing common electrical connections. The electrodes 170 may measure electrical characteristics, e.g., resistance, capacitance, etc. The electrodes 170 may measure thermal conductance in some embodiments. As described above, measuring the electrical characteristics and/or thermal conductance and comparing the measured value(s) to measured value when no unwanted liquid is present can be used to determine whether unwanted liquid is present. The measurements with no unwanted liquid present may be performed in a controlled environment and prior to field use where the measurement values are stored for comparison when the device is used in the field.

In some embodiments, the electrodes 170 are a pair of looped wires sharing the same electrical connections but have a separation around their midpoint. As such, the gap in between the pair of wires can measure a change in permeability when unwanted liquid is present. In some embodiments, the pair of wires may measure the permeability when unwanted liquid is absent (i.e. during a controlled measurement prior to field use). The permeability may be:

$$C = \varepsilon_0 \frac{A}{d}.$$

In contrast, when unwanted liquid is present, the permeability changes and can be measures by:

$$C = \varepsilon_1 \frac{A}{d}.$$

Referring now to FIG. 2B, an embodiment similar to that of FIG. 2A is shown except that multiple pairs of looped wires are used. For example, electrodes 170, 172, 174, and 176 are used. Each pair of electrodes in this embodiment have a different height, therefore detect a different amount of unwanted liquid within the internal environment 154 of the housing unit 150. For example, electrodes 176 detect a larger amount of unwanted liquid in comparison to the other electrodes because the electrodes 176 have the greatest height. In comparison electrodes 170 detect a larger amount of unwanted liquid in comparison to the electrodes 172 and 174 because the electrodes 170 have a height greater than electrodes 172 and 174. Moreover, electrodes 172 detect a larger amount of unwanted liquid in comparison to the electrodes 174 because the electrodes 172 have a height greater than that of electrodes 174.

Figure 3:
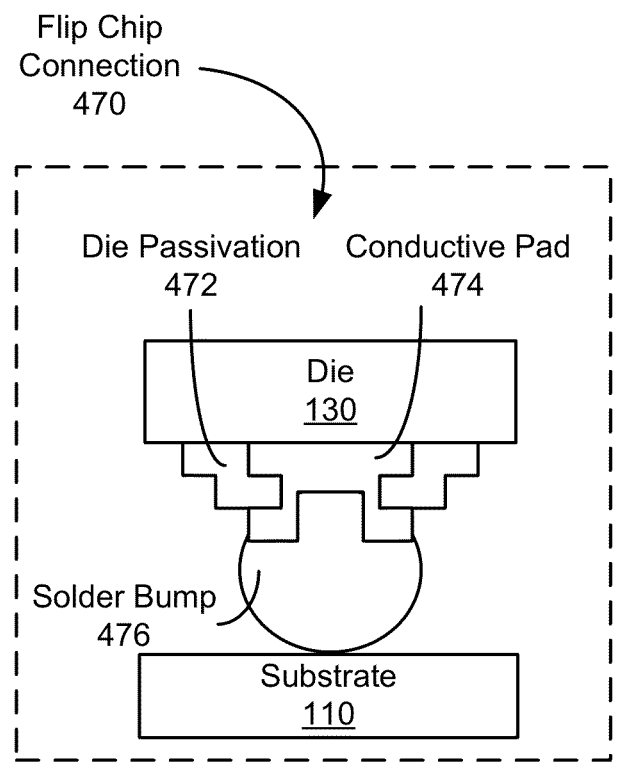
FIG. 3 shows a device with a flip chip die in accordance with some embodiments.

Referring now to FIG. 3, the device of FIGS. 1, 2A-2B is shown where the die 130 is coupled to the substrate using flip chip connection instead of wire bonds 132. In this embodiment, the die 130 may be a flip chip and electrically and mechanically connected to the substrate through die attach 120. More specifically the flip chip connection 470 connects the die 130 to the substrate 110. In some embodiments, the flip chip connection 470 includes a conductive pad 474 for electrically connecting the die 130 to the substrate 110. A die passivation layer 472 overlays the die 130 and the conductive pad 474. Solder bumps 476 are formed over the conductive pad 474. Optionally, die attach 120 can include mechanical attachment such as RTV or other soft material in addition to solder balls. It is appreciated that the housing unit 150 may house at least some of the exterior surfaces of the substrate 110, e.g., bottom surface, side surfaces, or any combination thereof, etc. In this embodiment, the housing unit 150 along with the die 130, die attach 120, and the gel 160 encapsulates the substrate 110.

Figure 4A:
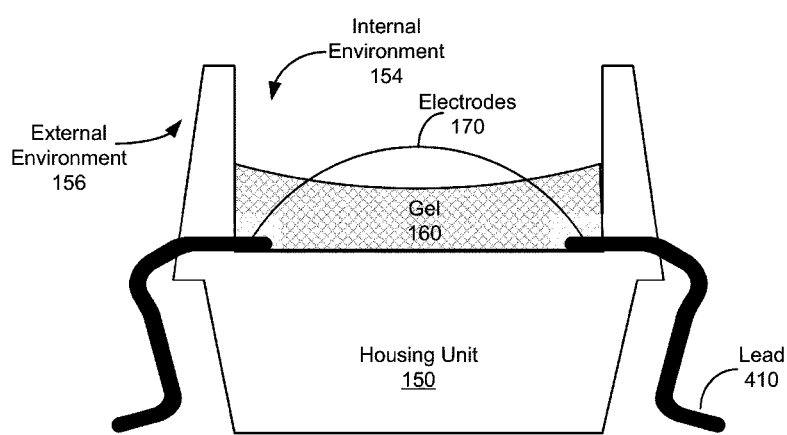
FIGS. 4A-4C show a cross view, a top view of a device with electrodes without unwanted liquid and a cross view of a device with electrodes with unwanted liquid in accordance with some embodiments.

Referring now to FIG. 4A, shows an alternative device in accordance with some embodiments. In this embodiment, the electrodes 170 are connected to leads 410 of the package directly instead of being connected to the die 130. In this embodiment, the electrodes 170 detect presence of unwanted liquid, as discussed above. It is appreciated that connecting the electrodes 170 to the leads 410 is for illustrative purposes and should not be construed as limiting the scope. For example, as discussed earlier, the electrodes 170 may be connected to the die 130. It is also appreciated that in FIG. 4A, the underlying die 130, the die attach 120, and substrate 110 are not shown but are present.

Figure 4B:
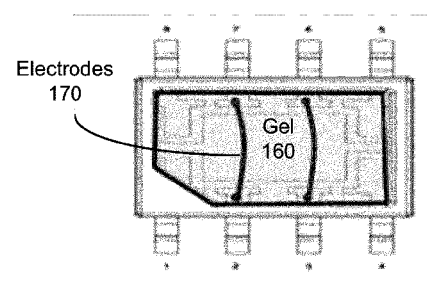
Figure 4C:
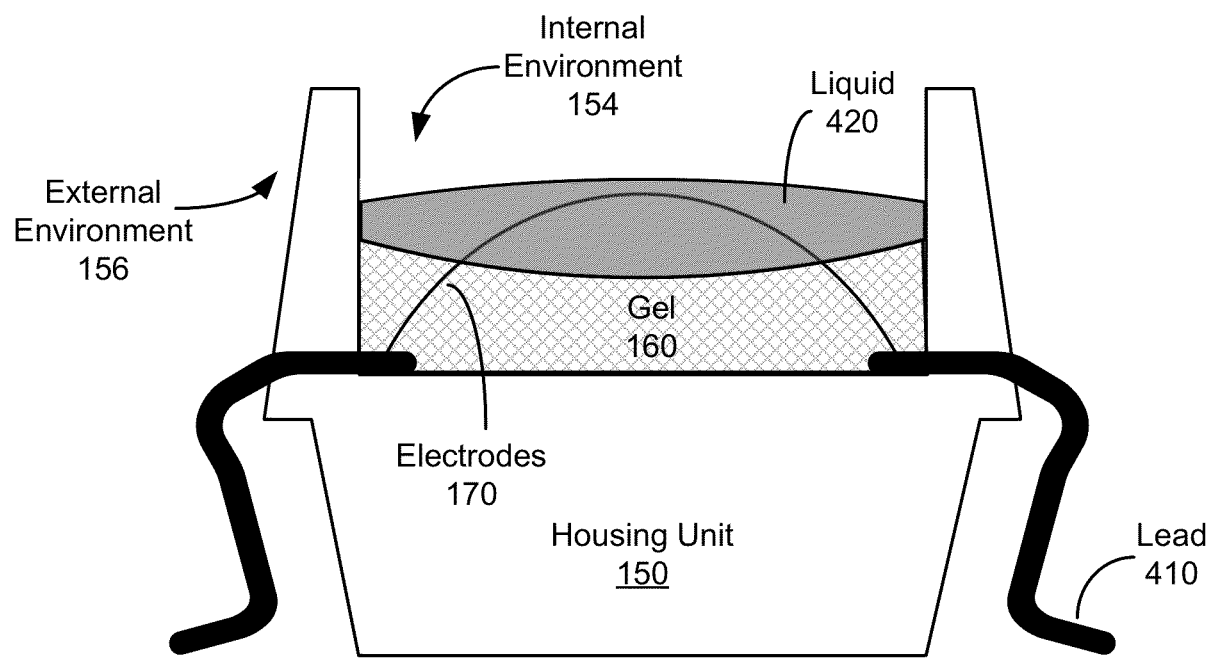

Referring now to FIG. 4B, a top view of the device as shown in FIG. 4A is illustrated. As shown, the electrodes 170 may be a pair of looped wires that are parallel to one another. As such, when unwanted liquid is present, the electrical characteristics, the measured thermal conductivity, etc., as measured by the electrodes 170 change because the characteristics of the material between the two electrodes 170 change. Referring now to FIG. 4C, the device as shown in FIG. 4A is shown in presence of unwanted liquid 420.

Figure 5:
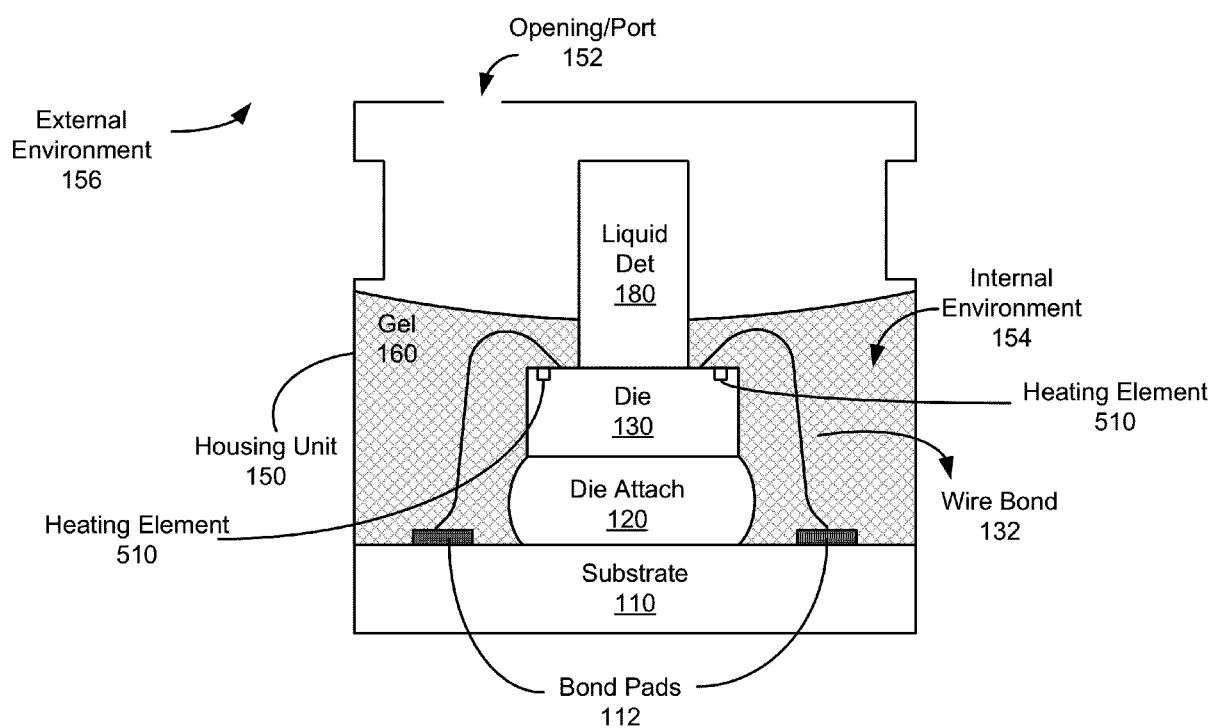
FIG. 5 shows a device with liquid detection unit and a heating element to take remedial action responsive to detecting unwanted liquid in accordance with some embodiments.

Referring now to FIG. 5, a device with liquid detection unit and a heating element to take remedial action responsive to detecting unwanted liquid in accordance with some embodiments is shown. The device in FIG. 5 is substantially similar to that of FIG. 1. In this embodiment, however, the die 130 includes a heating element 510 instead of being within the liquid detection unit 180. The heating element 510 generates heat. The liquid detection unit 180 may detect presence of unwanted liquid by causing the heating element 510 to apply a predetermined temperature, e.g., 10° C. The liquid detection unit 180 measures the amount of time that it takes for a temperature sensor (for example within the liquid detection unit 180 or within the die 130) to measure a predetermined temperature. The liquid detection unit 180 compares the measured amount of time to the amount of time that it takes to measure the predetermined temperature in absence of the unwanted liquid. If the difference in the amount of time is greater than a threshold then the liquid detection unit 180 may determine that unwanted liquid is present.

According to some embodiment, in response to detecting the unwanted liquid is present, remedial action is taken. The control circuitry (e.g., within the die 130) is configured to turn the heating element 510 on and maintain a temperature at a predetermined temperature responsive to the liquid detection unit 180 determining that liquid is present until the liquid is evaporated or until the liquid detection unit 180 determines that no more unwanted liquid is present.

It is appreciated that the heating element 510 may also be used to compensate for a drift in the sensor. For example, the control circuitry turns the heating element on to maintain a predetermined temperature in response to detecting that output from the sensor die has drifted. It is appreciated that the heating element 510 may be disposed within a plane of the movable membrane of the sensor (within the die 130). In some embodiments, the heating element 510 is disposed around the movable membrane of the sensor (within the die 130). It is appreciated that the heating element 510 may include silicon, metal, etc.

Figure 6:
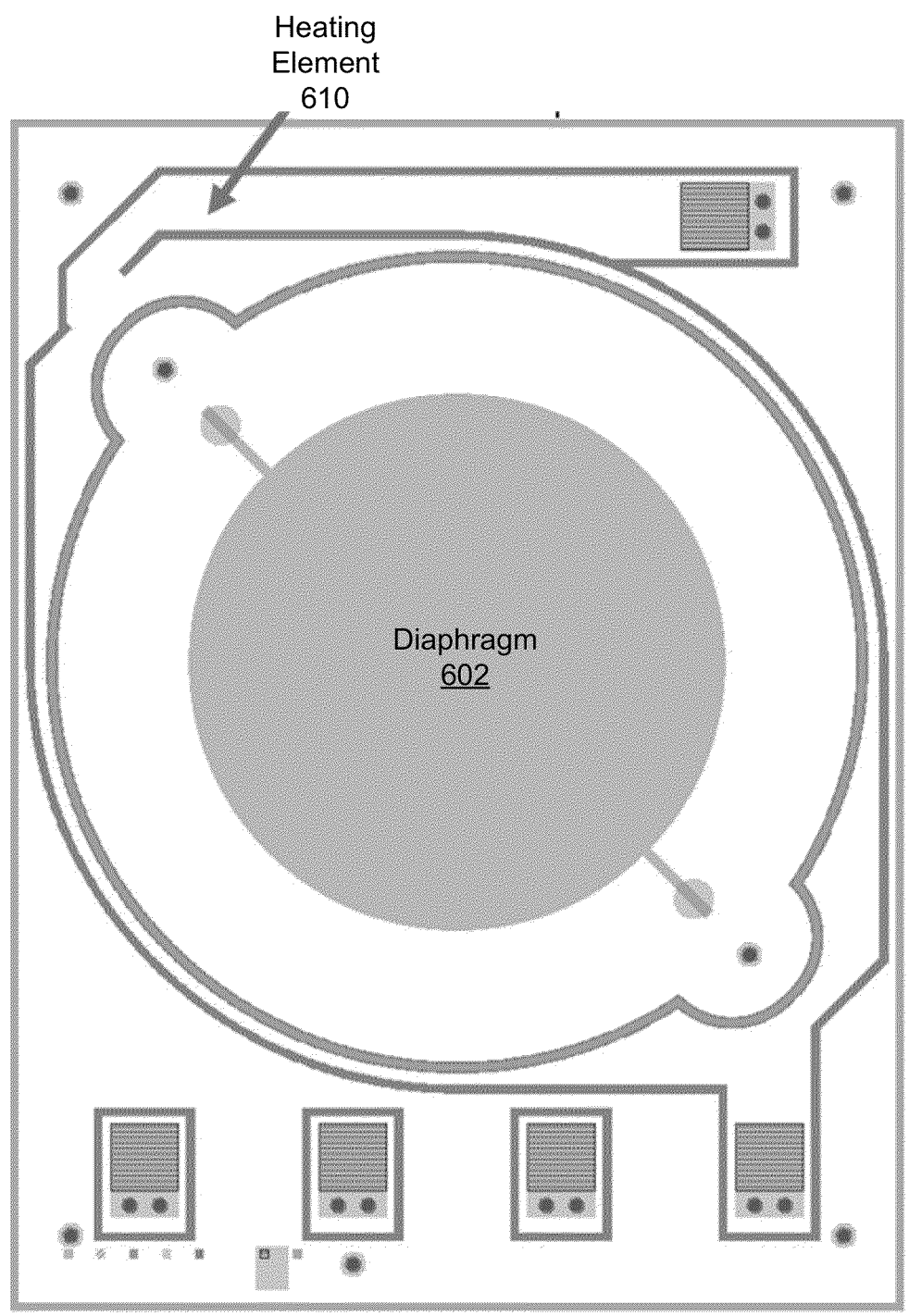
FIG. 6 shows a top view of a heating element for taking remedial action responsive to detecting unwanted liquid in accordance with some embodiments.

Referring now to FIG. 6, a top view of a heating element for taking remedial action responsive to detecting unwanted liquid in accordance with some embodiments is shown. In this embodiment, the heating element 610 which is substantially similar to heating element 510, is disposed around the movable membrane of the sensor, e.g., around the diaphragm 602. It is appreciated that the heating element 610 may form any shape and the illustrated shape around the diaphragm 602 and the shown configuration is for illustrative purposes only and should not be construed as limiting the scope of the embodiments.

While the embodiments have been described and/or illustrated by means of particular examples, and while these embodiments and/or examples have been described in considerable detail, it is not the intention of the Applicants to restrict or in any way limit the scope of the embodiments to such detail. Additional adaptations and/or modifications of the embodiments may readily appear to persons having ordinary skill in the art to which the embodiments pertain, and, in its broader aspects, the embodiments may encompass these adaptations and/or modifications. Accordingly, departures may be made from the foregoing embodiments and/or examples without departing from the scope of the concepts described herein. The implementations described above and other implementations are within the scope of the following claims.

What is claimed is:

1. A device comprising:
a housing unit with an internal volume;
a sensor coupled to a substrate via an electrical coupling, wherein the sensor is disposed within the internal volume of the housing unit, and wherein the sensor is in communication with an external environment of the housing unit from a side other than a side associated with the substrate; and
a moisture detection unit electrically coupled to the sensor, wherein the moisture detection unit comprises at least two looped wires at different heights, and wherein the moisture detection unit is configured to detect presence of a moisture within an interior environment of the housing unit when the moisture detection unit becomes in direct contact with the moisture.

2. The device of claim 1 further comprising a gel filled within the interior environment of the housing unit covering the sensor and the substrate, wherein the gel is configured to protect the sensor, the electrical coupling, and the substrate from exposure to the moisture.

3. The device of claim 2, wherein the gel is selected from a group consisting of silicone and fluoro silicone.

4. The device of claim 1, wherein the moisture detection unit comprises electrodes, wherein presence of moisture is detected responsive to a change in thermal conductance measured by the electrodes or responsive to a change of capacitance between the electrodes.

5. The device of claim 4, wherein the change in the thermal conductance is measured by measuring a resistance between the electrodes and by comparing the measured resistance to a resistance between the electrodes in absence of the moisture.

6. The device of claim 1, wherein the moisture detection unit comprises electrodes and wherein the moisture detection unit is within the sensor and is configured to detect presence of moisture by detecting a change in a measured electrical characteristics by the electrodes.

7. The device of claim 1, wherein the sensor is a pressure sensor.

8. The device of claim 1, wherein a pair of looped wires of the plurality of looped wires at a first height is configured to detect a different amount of moisture presence from another pair of looped wires of the plurality of looped wires at a second height.

9. The device of claim 1, wherein the moisture detection unit transmits the measured capacitance to the sensor for processing and determining whether moisture is present.

10. The device of claim 1, wherein the moisture detection unit transmits data to the sensor for processing and determining whether moisture is present.

11. The device of claim 1, wherein the moisture detection unit is configured to detect presence of moisture responsive to detecting a change in output from the sensor to a calibrated model.

12. The device of claim 1, wherein the moisture detection unit is further configured to measure a change in permeability.

13. A device comprising:
a housing unit with an internal volume;
a sensor comprising a heating element configured to generate heat, wherein the sensor is coupled to a substrate via an electrical coupling, wherein the sensor is disposed within the internal volume of the housing unit, and wherein the sensor is in communication with an external environment of the housing unit from a side other than a side associated with the substrate; and
a moisture detection unit electrically coupled to the sensor, wherein the moisture detection unit comprises at least two looped wires at different heights, and wherein the moisture detection unit is configured to detect presence of a moisture within an interior environment of the housing unit when the moisture detection unit becomes in direct contact with the moisture, and wherein a control circuitry within the sensor is configured to turn on the heating element responsive to the moisture detection circuitry detecting presence of moisture.

14. The device of claim 13 further comprising a gel filled within the interior environment of the housing unit covering the sensor and the substrate, wherein the gel is configured to protect the sensor die and the substrate from exposure to the moisture.

15. The device of claim 13, wherein the control circuity turns the heating element on to maintain a predetermined temperature in response to detecting that output from the sensor has drifted, and wherein maintaining the predetermined temperature compensates for the drift.

16. The device of claim 13, wherein the sensor comprises a pressure sensor, and wherein the heating element is disposed in a plane of a movable membrane of the pressure sensor.

17. The device of claim 16, wherein the heating element is disposed around the movable membrane.

18. The device of claim 17, wherein the heating element comprises silicon.

19. The device of claim 13, wherein applying heat responsive to detecting presence of moisture evaporates the moisture from the housing unit.

20. The device of claim 13, wherein the moisture detection unit comprises a temperature sensor and, wherein the moisture detection unit is configured to measure an amount of time elapsed until the temperature sensor determines that a predetermined temperature is reached, and wherein presence of moisture is detected responsive to a difference between the amount of time elapsed as measured by the moisture detection circuitry and an amount of time elapsed to reach the predetermined temperature in absence of liquid is greater than a threshold.

21. The device of claim 13, wherein the moisture detection unit further comprises a control circuitry configured to turn the heating element on and maintain a temperature at a predetermined temperature responsive to the moisture detection unit determining that moisture is present until the moisture detection unit determines absence of moisture.

\* \* \* \* \*